US012758163B2

(12) United States Patent
Liu

(10) Patent No.: US 12,758,163 B2
(45) Date of Patent: Oct. 13, 2026

(54) METHOD AND DEVICE OF DYNAMIC PET SCANNING, AND COMPUTER APPARATUS

(71) Applicant: SHANGHAI UNITED IMAGING HEALTHCARE CO., LTD., Shanghai (CN)

(72) Inventor: Shi-Tao Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 559 days.

(21) Appl. No.: 18/276,253

(22) PCT Filed: Feb. 8, 2022

(86) PCT No.: PCT/CN2022/075536
§ 371 (c)(1),
(2) Date: Aug. 8, 2023

(87) PCT Pub. No.: WO2022/166988
PCT Pub. Date: Aug. 11, 2022

(65) Prior Publication Data

US 2024/0115218 A1 Apr. 11, 2024

(30) Foreign Application Priority Data

Feb. 8, 2021 (CN) ........................ 202110170564.X

(51) Int. Cl.
*A61B 6/03* (2006.01)
*A61B 6/00* (2006.01)

(52) U.S. Cl.
CPC .............. *A61B 6/037* (2013.01); *A61B 6/488* (2013.01); *A61B 6/5217* (2013.01); *A61B 6/5294* (2013.01); *A61B 6/545* (2013.01)

(58) Field of Classification Search
None
See application file for complete search history.

(56) References Cited

U.S. PATENT DOCUMENTS

| | | | |
|---|---|---|---|
| 9,958,559 | B1 | 5/2018 | Feng et al. |
| 2007/0106154 | A1 | 5/2007 | Conti |

(Continued)

FOREIGN PATENT DOCUMENTS

| | | | |
|---|---|---|---|
| CN | 102920470 A | 2/2013 |
| CN | 105411618 A | 3/2016 |

(Continued)

OTHER PUBLICATIONS

Search Report of EP22749267.5.
International Search Report of PCT/CN2022/075536.

*Primary Examiner* — Hoon K Song

(57) ABSTRACT

Disclosed are a method and a device of dynamic PET scanning, and a computer apparatus. The method includes: performing a PET scan on a target region of a scanned object, and acquiring first PET-scan data including a single-event count received by a PET detector (S101); determining a single-event count distribution in the target region according to the first PET-scan data (S102); adjusting a position of a scanning table according to the single-event count distribution (S103); and performing a PET scan on the scanned object according to the adjusted position of the scanning table (S104). The method achieves a dynamic correlation between the position of the scanning table and changes of a tracer within the scanned object, so that more accurate scanned data can be obtained.

19 Claims, 2 Drawing Sheets

(56) References Cited

U.S. PATENT DOCUMENTS

| | | | | |
|---|---|---|---|---|
| 2011/0127434 | A1 * | 6/2011 | Wollenweber ......... | A61B 6/587 250/363.04 |
| 2020/0151918 | A1 | 5/2020 | Watson et al. | |

FOREIGN PATENT DOCUMENTS

| | | | |
|---|---|---|---|
| CN | 105792888 | A | 7/2016 |
| CN | 106023278 | A | 10/2016 |
| CN | 106466186 | A | 3/2017 |
| CN | 106539591 | A | 3/2017 |
| CN | 106556857 | A | 4/2017 |
| CN | 107095691 | A | 8/2017 |
| CN | 109031395 | A | 12/2018 |
| CN | 109480883 | A | 3/2019 |
| CN | 111887878 | A | 11/2020 |
| CN | 111904379 | A | 11/2020 |
| CN | 112006713 | A | 12/2020 |
| CN | 112971824 | A | 6/2021 |
| WO | WO2017024451 | A1 | 2/2017 |

* cited by examiner

METHOD AND DEVICE OF DYNAMIC PET SCANNING, AND COMPUTER APPARATUS

CROSS-REFERENCE TO RELATED APPLICATION

The present application is a U.S. National Stage of International Application No. PCT/CN2022/075536, filed on Feb. 8, 2022, which claims priority to Chinese patent application No. 202110170564.X, entitled “Method and Device of Dynamic PET Image Scanning, And Computer Apparatus”, filed on Feb. 8, 2021, which is incorporated herein by reference in its entirety.

TECHNICAL FIELD

The present application relates to the technical field of medical imaging, particularly to a method and a device of dynamic PET scanning, and a computer apparatus.

BACKGROUND

PET (Positron Emission Tomography) allows performing a PET scan on a subject within an effective field of view of a PET system by labeling a positron-emitting radionuclide (i.e., a tracer) onto a compound capable of participating in a blood flow or a metabolism of human tissues, and by injecting the compound into the subject. The positrons emitted by the radionuclide combine with negatrons in tissues in the human body, and an annihilation radiation is generated, producing two y photons with equal energy and moving in opposite directions. The PET system may detect y photon pairs by means of a detection device thereof, and reconstruct a dynamic image reflecting the metabolic status of each tissue of the organism, so as to track dynamic physiological processes of human tissues and organs.

In medical imaging, dynamic imaging is often used to view the metabolism of the tracer in the human body, so as to analyze functions of the organs more accurately. In dynamic imaging, imaging needs to be performed throughout the process from injecting the tracer to distributing the tracer through metabolism, and the whole body is involved in this process. Therefore, when the field of view of the PET system cannot cover the whole body, it is difficult to acquire accurate scanned data. A conventional dynamic imaging method performs dynamic imaging by an examination table carrying a patient to make a periodic reciprocating motion, and all parts of the human body are imaged in turn and at a constant speed, such that a dynamic process is constructed by concatenating discontinuous time points, and is not related to the dynamics of the tracer itself, so that key metabolism information is easily omitted, and that a good imaging effect cannot be achieved.

SUMMARY

The present application provides a method and a device of dynamic PET scanning, and a computer apparatus, to solve at least the problem that key metabolism information is easily omitted in the dynamic scanning methods in the related art.

In a first aspect, the embodiment of the present application provides a method of dynamic PET scanning, including:

- performing a PET scan on a target region of a scanned object, and acquiring first PET-scan data, the first PET-scan data including a single-event count received by a PET detector;

- determining a single-event count distribution in the target region according to the first PET-scan data;
- adjusting a position of a scanning table according to the single-event count distribution; and
- performing a PET scan on the scanned object according to the adjusted position of the scanning table.

In some of these embodiments, the acquiring the first PET-scan data includes:

- acquiring the first PET-scan data of the scanned object in real time or at a preset time point within a certain time period after injecting a tracer.

In some of these embodiments, the first PET-scan data include the number of coincidence events received by the crystal ring at different time points.

A position of a scanning table is adjusted according to the number of coincidence events.

A PET scan is performed on the scanned object according to the adjusted position of the scanning table.

In some of these embodiments, the first PET-scan data include coincidence counting rates of the crystal rings at different time points, and each of the coincidence counting rates represents the number of coincidence events received by a single-crystal ring in a PET detector per unit time.

The adjusting the position of the scanning table according to the number of coincidence events includes:

- adjusting the position of the scanning table according to the coincidence counting rates.

In some of these embodiments, the adjusting the position of the scanning table according to the coincidence counting rates includes:

- determining whether a coincidence counting rate of each of the crystal rings is greater than a preset threshold value or not; and
- adjusting the position of the scanning table according to a position of a crystal ring having the coincidence counting rate greater than the preset threshold value.

In some of these embodiments, the adjusting the position of the scanning table according to the coincidence counting rates includes:

- determining a maximum coincidence counting rate of the crystal rings; and
- adjusting the position of the scanning table according to a position of a crystal ring having the maximum coincidence counting rate.

In some of these embodiments, the adjusting the position of the scanning table according to the position of the crystal ring having the coincidence counting rate greater than the preset threshold value, includes:

- moving a position of a scanned object part, which corresponds to the crystal ring having the coincidence counting rate greater than the preset threshold value, to a scanning center.

In some of these embodiments, at a last position among multiple positions of the scanning table, a scanning range at least includes a region of interest of the scanned object.

In some of these embodiments, at the last position among the multiple positions of the scanning table, a geometric center of the region of interest of the scanned object is at the scanning center.

In some of these embodiments, the region of interest includes a heart position of the scanned object.

In some of these embodiments, the method of dynamic PET scanning further includes:

- acquiring the region of interest, and adjusting the position of the scanning table according to a position of the region of interest and a position of the target region.

In some of these embodiments, the method further includes:

performing a PET scan on the target region of the scanned object at a plurality of positions of the scanning table to acquire second PET-scan data;

reconstructing a PET image according to the second PET-scan data; and acquiring a PET parametric image according to the PET image.

In some of these embodiments, the method further includes:

performing a PET scan on the target region of the scanned object at a plurality of positions of the scanning table to acquire the second PET-scan data;

reconstructing the PET image according to the second PET-scan data;

determining at least one scanning parameter according to the PET image; and performing another PET scan on the target region of the scanned object according to the scanning parameter to acquire third PET-scan data.

In some of these embodiments, the target region includes a partial region of the scanned object.

In a second aspect, the embodiment of the present application provides a device of dynamic PET scanning including:

a first data acquiring unit, configured to perform a PET scan on a target region of a scanned object, and acquire first PET-scan data, wherein the first PET-scan data comprises a single-event count received by a PET detector;

a data processing unit, configured to determine a single-event count distribution in the target region according to the first PET-scan data;

a scanning table adjusting unit, configured to adjust a position of a scanning table according to the single-event count distribution; and a scan unit, configured to perform a PET scan on the scanned object according to the adjusted position of the scanning table.

In a third aspect, the present application provides a computer apparatus, including a memory, a processor, and a computer program stored in the memory and executable by the processor. The processor, when executing the computer program, performs the method of dynamic PET scanning according to the first aspect.

Compared with the related art, the method of dynamic PET scanning provided in the embodiment of the present application performs the PET scan on the target region of the scanned object after injecting the tracer into the scanned object to acquire the first PET-scan data, thereby determining the single-event count distribution in the target region, and tracing the transmission and metabolism of the tracer in different parts of the scanned object. By adjusting the position of the scanning table according to the single-event count distribution, and performing the PET scan on the scanned object at the adjusted position of the scanning table, the position of the scanning table is dynamically correlated with the change of the tracer in the scanned object. Therefore, regardless of whether the field of view of the PET system can cover the whole body of the scanned object or not, the dynamic scanning for the transmission and metabolism of the tracer in the human body can be performed by changing the position of the scanning table, so that more accurate scanned data can be obtained.

The details of one or more embodiments of the present application are provided in the accompanying drawings and the description hereinafter, so that other features, objectives, and advantages of the present application are more comprehensible.

BRIEF DESCRIPTION OF THE DRAWINGS

The accompanying drawings that constitute part of the present application are provided to make the present application to be further understood. The illustrative embodiments of the present application as well as the description thereof are provided to explain the present application, but not intended to constitute improper limitations to the present application. In the drawings.

Figure 1:
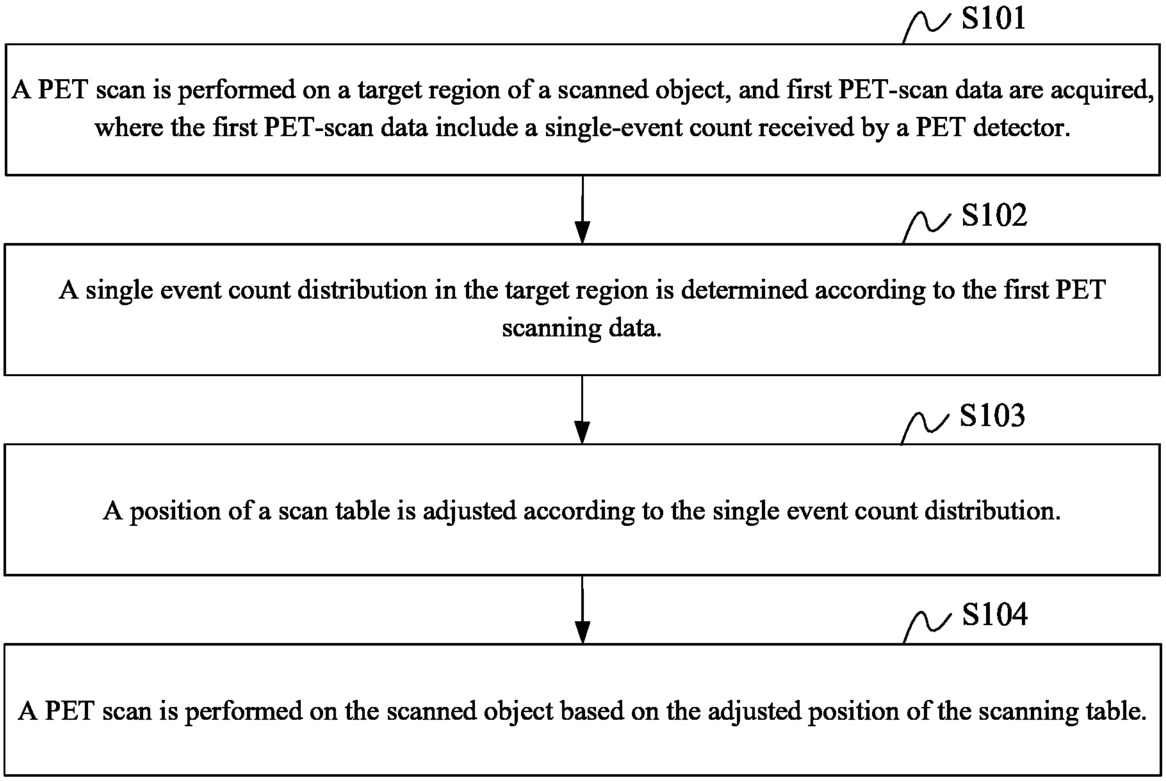
FIG. 1 is a schematic flow chart of a method of dynamic PET scanning in one of the embodiments of the present application.

Reference Numerals: 301, first data acquiring unit; 302, data processing unit; 303, scanning table adjusting unit; 304, scan unit; 50, bus; 51, processor; 52, memory; and 53, communication interface.

DETAILED DESCRIPTION OF THE EMBODIMENTS

In order to make the objectives, technical solutions, and advantages of the present application clearer and better understood, the present application is described and illustrated below combining with the accompanying drawings and embodiments. It should be understood that specific embodiments described herein are only intended to explain the application but not intended to limit the application. All other embodiments obtained by those of ordinary skill in the art based on the embodiments of the application without involving creative efforts fall within the protection scope of the application.

Obviously, the accompanying drawings in the following description are merely some examples or embodiments of the application. For those of ordinary skill in the art, the present application may also be applied to other similar scenarios based on these accompanying drawings without involving creative efforts. In addition, it should be understood that although the efforts made in a development process may be complicated and lengthy, for those of ordinary skill in the art related to the disclosure of the present application, some designs, manufacturing, or production changes made on the basis of the technology disclosed in the present application, are only conventional technical means, and should not be understood as contents insufficiently disclosed in the present application.

The term “embodiment” mentioned in the present application means that specific features, structures or characteristics, which are described combining with the embodiments, may be included in at least one embodiment of the application. This term described at various places in the description does not necessarily refer to the same embodiment, nor is it an independent or an alternative embodiment mutually exclusive with other embodiments. It is understood explicitly and implicitly by those of ordinary skill in the art that, if no confliction occurs, the embodiments described in the application may be combined with other embodiments.

Unless otherwise defined, the technical terms or scientific terms involved in the application shall have general meanings as understood by those of ordinary skill in the related art. The terms "a", "an", "one", "the", and the like in the application do not imply a limitation to the quantity, and may denote the singular or plural ones. The terms "comprise", "include", "have", and any variation thereof in the application are intended to cover non-exclusive inclusion. For example, a process, a method, a system, a product, or a device, which includes a series of steps or components (units), is not limited to the listed steps or units, but may also include steps or units that are not listed, or may also include other steps or units inherent to the process, the method, the product or the device. The terms "connect", "communicate", "couple", and the like in the application, are not limited to a physical or mechanical connection, but may include an electrical connection, whether it is direct or indirect. The "plurality" referred to in the application refers to a number of two or more. "And/or" describes an association relationship of associated objects, and means that there may be three kinds of relationships. For example, "A and/or B" may indicate that there are three situations: A alone, A and B together, and B alone. The character "/" generally indicates that the associated objects are in an "or" relationship. The terms "first", "second", "third", and the like in the application are merely used to distinguish similar objects, but do not represent a specific ordering of the objects.

A PET scan system uses radioactive tracing principle for imaging. By displaying the biochemical status of living tissues and organs, it reflects the relevant functional information of human metabolism, such as the degree of metabolic activity in the tissue. Therefore, physiological and biochemical changes of metabolites entering the human body can be observed non-invasively and dynamically at a molecular level, and has the characteristics of being quantifiable and highly sensitive.

The present application provides a method of dynamic PET scanning FIG. 1 is a flow chart of the method of dynamic PET scanning in accordance with an embodiment of the present application. As shown in FIG. 1, the method includes the following steps.

At step S101, a PET scan is performed on a target region of a scanned object, and first PET-scan data are acquired, where the first PET-scan data include a single-event count received by a PET detector.

In the present embodiment, the target region is a region of the scanned object, where the PET scan needs to be performed. The target region may be a head, a neck, a chest, an abdomen, a leg, or the like, or any combination thereof. The detector of the PET scan system consists of a plurality of ring-shaped crystal rings, all of which have corresponding position information. In the process of performing the PET scan, when positrons generated by the decay of radionuclides collide with negatrons, an annihilation is generated, then a pair of photons moving in opposite directions are formed. The PET scan system detects a photon pair that meets the conditions (where a time window is generally required to be less than or equal to 15 ns) by means of the detector based on the features of the annihilation radiation and the coincidence of two output pulses of the detector. After the PET detector receives a photon incident, the PET detector generates a corresponding electrical signal. Receiving one photon is a single-event. The photons received by the PET detector are counted to obtain a single-event count.

At step S102, a single-event count distribution in the target region is determined according to the first PET-scan data.

In the present embodiment, the photons received by all of the crystal rings of the detector are counted and analyzed to obtain the single-event count distribution in the corresponding target region, so that the distribution of the tracer within the target subject may be determined.

At step S103, a position of a scanning table is adjusted according to the single-event count distribution.

At step S104, a PET scan is performed on the scanned object based on the adjusted position of the scanning table.

In the present embodiment, the distribution of the tracer in the target subject may be determined by using the single-event count distribution, based on which the position of the scanning table is adjusted. Further, a dynamic scan is performed on the transmission and metabolism of the tracer to obtain more accurate scanned data.

According to the method of dynamic PET scanning of the present embodiment, the PET scan is performed on the target region of the scanned object, the first PET-scan data are acquired, and the single-event count distribution in the target region is determined, thereby tracing the transmission and metabolism of the tracer in different parts of the scanned object. The position of the scanning table is adjusted according to the single-event count distribution, and the scanned object is scanned at the adjusted position of the scanning table, so that the position of the scanning table is dynamically correlated with the change of the tracer in the scanned object, thereby realizing an adaptive adjustment of the position of the scanning table according to the change of the tracer. Therefore, regardless of whether the field of view of the PET system can cover the whole body of the scanned object or not, the dynamic scanning for the transmission and metabolism of the tracer in the human body can be performed by changing the position of the scanning table, so that the scanned data can be more accurately correlated with the change of the tracer, thus key metabolism information is not omitted.

In some embodiments, the acquiring the first PET-scan data includes:

acquiring the first PET-scan data of the scanned object in real time or at a preset time point within a certain time period after injecting a tracer.

In the present embodiment, after the tracer is injected to the scanned object, the first PET-scan data may be determined according to a scanning range of the target region, that is, the first PET-scan data are acquired within the scanning range. Generally, in some embodiments, the scanning range may be determined based on a location where the tracer is injected into the scanned object, the position of the scanning table, or a region of interest (e.g., target organ). In other embodiments, a default scanning range may also be set.

Typically, when dynamic imaging is performed on the target organ, the certain time period covers at least a time period starting from the time, when the tracer is injected into the scanned object, to the time when the tracer arrives at the target organ. The target organ may be a head, neck, chest, heart, stomach, blood vessel, soft tissue, tumor, nodule, or the like, or any combination thereof. The preset time point is one of time points with a certain time interval therebetween within the certain time period. The scanning table is moved at the preset time point to perform the PET scan to obtain the first PET-scan data. For example, in the process starting from the tracer being injected into the intravenous to the tracer reaching the heart, the tracer reaches the neck of the scanned object at a first time point, and reaches the chest of the scanned object at a second time point. The first time point and/or the second time point may be set as the preset time point(s), and the PET scan is performed at the preset time period. Alternatively, the time interval may be a preset time interval. When there are multiple scan sequences, the time interval may also be a time interval between different scan sequences. The time intervals between adjacent time points may be identical or different. By using the first PET-scan data at the preset time point, the amount of scanned data may be reduced, and the position of the scanning table may be adjusted more quickly.

Alternatively, when dynamic imaging is performed on the target organ, a real-time PET scan is performed. The single-event count required for moving the position of the scanning table is provided in real time, the position of the scanning table is adjusted according to the single-event count distribution in the target region, and the PET scan is performed on the scanned object based on the scanning table moving in real-time. When the scanning table moves in real time, the positioning of the scanning table may be more accurately correlated with the change of the tracer, thereby realizing a real-time tracing of the transmission and metabolism of the tracer at different parts of the scanned object, and avoiding missing the key metabolism information. Moreover, when the tracer is injected into the scanned object, the table may be adjusted adaptively in real time according to the change of the single-event count regardless of whether the injection location of the tracer is within the scanning aperture or not. In particular, when the scanned object is injected with the tracer at a location beyond the scanning aperture, the function of moving the scanned object to the center of the scanning system may be realized through the automatic real-time positioning of the scanning table.

The tracer is a radionuclide such as 11C, 13N, 15O, 18F, etc. The radionuclide is unstable because it is rich in protons, and decay to produce positrons in order to reach a stable state. The positron continuously scatters in the surrounding medium and slows down. When the positron is at rest and collides with a negatron, a negatron-positron annihilation occurs to generate photon pairs. Image reconstruction and metabolic tracing are realized by detecting a coincidence of photons. In general, different radioactive tracers may trace and reflect different metabolisms and may be selected for use according to clinical needs. For example, brain-function imaging agents, heart-function imaging agents, positive-tumor imaging agents, etc., may be selected for use according to functions. The radioactive tracers may be categorized as metabolic imaging agents, binding imaging agents, and blood perfusion imaging agents according to biochemical action substances.

In some embodiments, the first PET-scan data include the number of coincidence events received by the crystal rings at different time points.

The position of the scanning table is adjusted according to the number of coincidence events.

The PET scan is performed on the scanned object according to the adjusted position of the scanning table.

In the present embodiment, the single-events received by the crystal rings may be used for coincidence calculation to obtain the number of coincidence events. As the tracer is transmitted and metabolized in the human body, the number of coincidence events received by the crystal rings changes at different time points. By adjusting the position of the scanning table according to the number of coincidence events, the change of the tracer can be accurately correlated without missing the key metabolism information.

In some embodiments, the first PET-scan data include coincidence counting rates of the crystal rings at different time points, and the coincidence counting rate represents the number of coincidence events received by a single-crystal ring in the PET detector per unit time.

The adjusting the position of the scanning table according to the number of coincidence events includes:

adjusting the position of the scanning table according to the coincidence counting rates.

In the present embodiment, by using the coincidence counting rates of the crystal rings at the different time points, the scanning table may be controlled more timely, so as to correlate with the change of the tracer more accurately.

It should be noted that the coincidence counting rates belong to at least one crystal ring. For a plurality of crystal rings, their coincidence counting rates at the time point may be obtained simultaneously.

In some embodiments, the coincidence counting rates of at least two crystal rings within a scanning range at different time points are obtained according to the first PET-scan data.

The position of the scanning table is adjusted according to the coincidence counting rates.

Specifically, the detector of the PET scan system consists of a plurality of ring-shaped crystal rings, all of which have corresponding position information. In the process of performing the PET scan, when positrons generated by the decay of radionuclides collide with negatrons, an annihilation is generated, then a pair of photons moving in opposite directions are formed. The PET scan system detects a photon pair that meets the conditions (where a time window is generally required to be less than or equal to 15 ns) by means of the detector based on the features of the annihilation radiation and the coincidence of two output pulses of the detector. After the PET detector receives a photon incident, the PET detector generates a corresponding electrical signal. A coincidence processing circuit of the PET detector performs a coincidence processing on the electrical signals to obtain a coincidence event, thereby obtaining the coincidence counting rates of the at least two crystal rings. The position of the tracer is determined by a line of response (LOR) formed by a measurement for coincidence, thereby determining the corresponding part of the scanned object.

It should be noted that the crystal ring may be a single-crystal ring including a plurality of crystal units in the detector, or may be a detector ring including a plurality of single-crystal rings.

After the tracer is injected into the scanned object, the accumulation position and concentration of the tracer in the scanned object change constantly, therefore the coincidence counting rate of each crystal ring of the detector changes constantly. After obtaining the coincidence counting rates of at least two crystal rings at different time points, the position of the scanning table is determined according to the numerical information of the coincidence counting rates, thus controlling the movement of the scanning table, and the required scanned data are obtained by switching from a passive observation to an active tracking, thereby enabling more accurate dynamic imaging.

In view of the above, according to the method of dynamic PET scanning provided in the embodiment of the present application, after the tracer is injected into the scanned object, the coincidence counting rates of at least two crystal rings in the scanning range are calculated according to the first PET-scan data at the preset time point in the certain time period, thereby realizing the tracing for the transmission and metabolism of the tracer in different parts of the scanned object. By adjusting the position of the scanning table according to the numerical information of the coincidence counting rates, the scanned object is scanned at the adjusted position of the scanning table, so that the positions of the scanning table are dynamically correlated with the change of the tracer in the scanned object at different time points. Therefore, regardless of whether the field of view of the PET system can cover the whole body of the scanned object or not, the dynamic scanning for the transmission and metabolism of the tracer in the human body can be performed by changing the position of the scanning table, thereby obtaining more accurate scanned data.

Embodiments of the present application are described and illustrated hereinafter by means of alternative embodiments.

In some of these embodiments, the adjusting the position of the scanning table according to the coincidence counting rates includes:

firstly, determining whether the coincidence counting rate of the crystal ring is greater than a preset threshold value or not. The detector includes a plurality of crystal rings, each of which receives coincidence events. During a scan of a different part, the coincidence counting rate of each crystal ring is calculated. A crystal ring, whose coincidence counting rate is greater than a preset threshold value, is selected, and the position of the corresponding crystal ring is determined, so as to provide a support for adjusting the position of the scanning table. The preset threshold value is a threshold value preset mainly based on the characteristics of the tracer and the scanning purpose, and is used to determine whether the concentration of the tracer is sufficiently high and whether a sufficiently large coincidence counting rate may be obtained.

Specifically, in the present embodiment, the maximum number of coincidence events received by a single-crystal ring in the detector is determined to be a maximum value, and a maximum value among the coincidence counting rates of all crystal rings is selected as a maximum coincidence counting rate.

Then, the position of the scanning table is adjusted according to the position of the crystal ring having the coincidence counting rate greater than the preset threshold value. In the present embodiment, all of the crystal rings in the detector have corresponding position information. When the detector receives a photon pair, a position information of the current corresponding crystal ring that receives the photons and photon information are recorded. The position information includes horizontal and vertical coordinates of the crystal ring in the entire detector structure. The photon information includes at least one of a photon position, a photon incident angle, a photon energy, a photon transmission time, and the number of photon pairs.

Specifically, if the maximum value of the coincidence counting rate is used, the position of the scanning table is adjusted according to the maximum coincidence counting rate.

It should be noted that the single-event count is also applicable, and that the position of the scanning table may be adjusted by using a single-event count greater than the preset threshold value, or by using or a maximum single-event count.

In some embodiments, the adjusting the position of the scanning table according to the position of the crystal ring having the coincidence counting rate greater than the preset threshold value, includes:

moving a position of a scanned object part, which corresponds to the crystal ring having the coincidence counting rate greater than the preset threshold value, to a scanning center.

In the present embodiment, determining the position of the part of the scanned object corresponding to the crystal ring having the coincidence counting rate greater than the preset threshold value includes: based on the position information of the crystal ring receiving the photons and the corresponding photon information, determining the position of the part of the scanned object corresponding to the position of the crystal ring having the coincidence counting rate greater than the preset threshold. Specifically, after another photon in the same photon pair of annihilation arrives at a crystal ring, the position information of the other photon may be acquired according to the position information of the current crystal ring that receives the photon, and the incident angle information of the received photon. A line is drawn according to the position information of the two crystal rings receiving the pair of photons to obtain information of a response line, thus determining a position of the corresponding annihilation event according to the response line of the coincident event. The position of the part of the scanned object, which corresponds to the position where the annihilation events are generated for the number of times larger than a preset threshold value, is moved to the scanning center.

Specifically, adjusting the position of the scanning table according to the maximum value includes: moving the position of the part of the scanned object corresponding to the maximum value to the scanning center of the PET system. Specifically, determining the position of the part of the scanned object corresponding to the maximum value includes: based on the position information of the crystal ring receiving the photon and the corresponding photon information, determining the position of the part of the scanned object corresponding to the maximum value. Specifically, after another photon in the same photon pair of annihilation arrives at a crystal ring, the position information of the other photon may be acquired according to the position information of the current crystal ring that receives the photon, and the incident angle information of the received photon. A line is drawn according to the position information of the two crystal rings receiving the pair of photons to obtain the information of a response line, thus determining a position of the corresponding annihilation event according to the response line of the coincident event. The position of the part of the scanned object, which corresponds to the position where the annihilation events are generated for a maximum number of times, is determined to be the position of the part of the scanned object corresponding to the maximum value.

It should be understood that, in other embodiments, adjusting the position of the scanning table according to the maximum value may be: moving the position of the part of the scanned object, which corresponds to the maximum value, to a preset range of the scanning range of the PET system, or setting the table position of the scanning table according to the position of the part of the scanned object corresponding to the maximum value, or the like.

On the basis of the above embodiments, in some of these embodiments, at a last position among multiple positions of the scanning table, the scanning range at least includes the region of interest of the scanned object.

In the present embodiment, starting from injecting the tracer into the scanned object, the tracer moves in the vein of the scanned object over time. The numerical information of the corresponding coincidence counting rate of the crystal ring continuously changes, and the corresponding position of the scanning table continuously changes. After being injected into the scanned object, the tracer gradually moves to the region of interest of the scanned object. At the last position among the multiple positions of the scanning table, the scanning range at least includes the region of interest of the scanned object, which is conducive to the detection purpose of the final imaging. The region of interest, such as lung, liver, spleen, stomach, kidney, intestine, brain, etc., may be selected according to actual needs.

In an embodiment, the method of dynamic PET scanning further includes:

acquiring a region of interest, and adjusting the position of the scanning table according to a position of the region of interest and a position of the target region.

In the present embodiment, in order to observe a correlation between the plurality of regions, such as the correlation between the brain and the intestine, a movement sequence of the table may be set according to the metabolic characteristics of the human body, and the scanning table is controlled to move between the region of interest and the target region, so that the PET system firstly images the brain region and then moves to image the intestinal region.

Further, at the last position among the multiple positions of the scanning table, a geometric center of the region of interest of the scanned object is at a scanning center. The geometric center of the region of interest is positioned at the scanning center, which is conducive to imaging of the entire region of interest.

Specifically, the region of interest may include the heart position. Starting from injecting the tracer into the scanned object, the tracer moves in the vein of the scanned object over time. The numerical information of the corresponding coincidence counting rate of the crystal ring continuously changes, and the corresponding position of the scanning table continuously changes in order to facilitate the tracing of the dynamic changing process of the tracer. The flow direction of the tracer in the blood circulation system is continuous and regular after the tracer is injected into the scanned object and before the tracer moves to the heart. However, after the tracer arrives at the heart, the tracer exhibits a divergent movement until it is evenly distributed along with the blood in the body. At the last position among the multiple positions of the scanning table, the scanning range at least includes the heart position of the scanned object, and tracing the transmission and metabolism of the tracer before it moves to the heart has a greater clinical significance. Alternatively, in order to observe the dynamic changing process of the tracer starting from injecting the tracer into the vein to the tracer arriving at the heart, at the last position among the multiple positions of the scanning table, a geometric center of the heart position of the scanned object is at the scanning center of the PET system.

Figure 2:
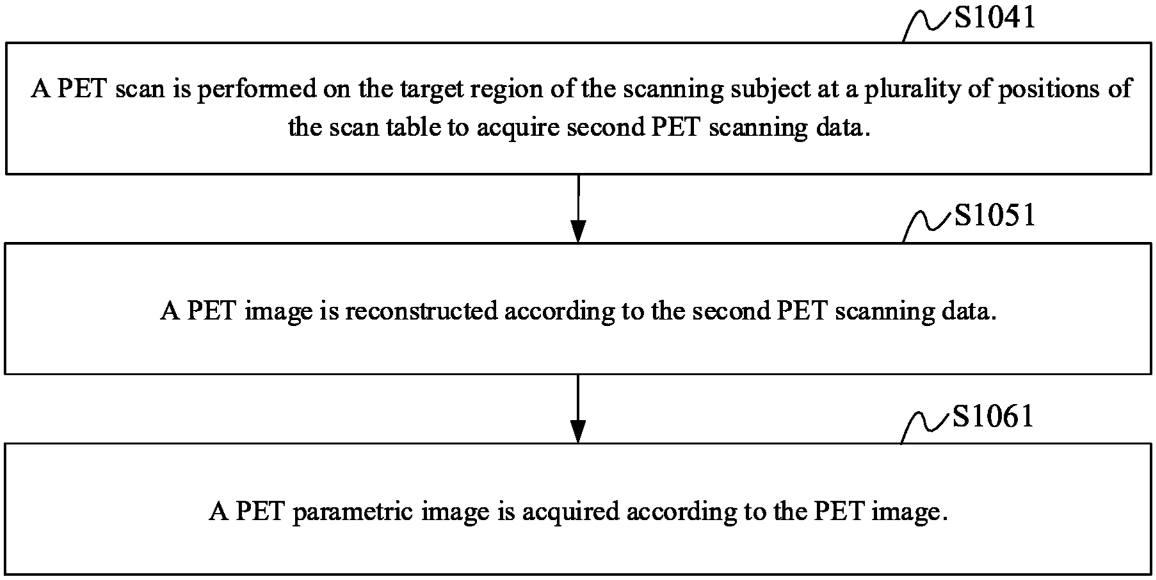
FIG. 2 is a schematic flow chart of acquiring a PET parametric image in one of the embodiments of the present application.

As shown in FIG. 2, on the basis of the above embodiments, in some of these embodiments, the method further includes the following steps.

At step S1041, a PET scan is performed on the target region of the scanned object at a plurality of positions of the scanning table to acquire second PET-scan data.

At step S1051, a PET image is reconstructed according to the second PET-scan data.

At step S1061, a PET parametric image is acquired according to the PET image.

In the present embodiment, the position of the scanning table is adjusted according to the single-event count, and the scanned object is scanned at the plurality of positions of the scanning table therefore the scanning process is closely correlated with the transmission and metabolism of the tracer without missing the key metabolism information, thereby obtaining the scanned data of the target organ in the whole process, which starts from injecting of the tracer to being distributed through metabolism. When the image reconstruction is performed based on the second PET-scan data, a conventional reconstruction algorithm, such as a filtered back-projection (FBP) algorithm, or an iterative algorithm, may be used to reconstruct image frames. The image reconstruction algorithm is not limited in the present embodiment. For example, the selected second PET-scan data may be segmented to obtain PET-scan data corresponding to each PET image frame, and then the PET-scan data corresponding to each PET image frame may be reconstructed to obtain the PET image.

It should be noted that the first PET-scan data are used to provide a support for controlling the movement of the scanning table, and the second PET-scan data are used to reconstruct the PET image.

In the present embodiment, the PET image is a PET dynamic image composed of multiple frames of image. The PET dynamic image can not only display a spatial distribution of the concentration of the tracer, but also display the dynamic process of the metabolism of the tracer over time. After the PET image is obtained, the PET parametric image is reconstructed based on a plasma input function derived from the PET dynamic image. A time-activity curve may also be fitted based on the reconstructed PET image to obtain the time-activity curve, and the PET parameter imaging may be performed based on the time-activity curve. The PET parametric image may indicate some physiological parameters (also referred to as kinetic parameters) of the tracer, which is conducive to estimation of the physiological (functional) and/or anatomical (structural) properties, and biochemical properties of the targeted organ or tissue.

Figure 3:
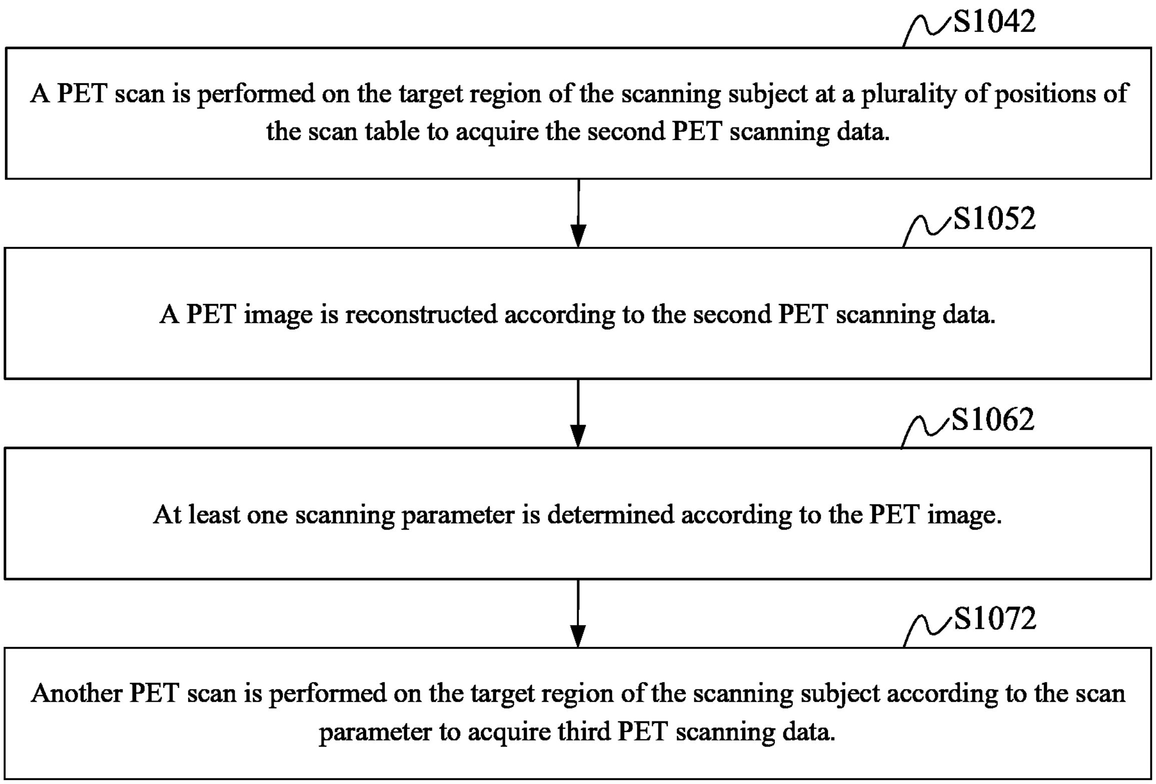
FIG. 3 is a schematic flow chart of acquiring third PET-scan data in one of the embodiments of the present application.

As shown in FIG. 3, on the basis of the above embodiments, in some of these embodiments, the method further includes the following steps.

At step S1042, a PET scan is performed on the target region of the scanned object at a plurality of positions of the scanning table to acquire the second PET-scan data.

At step S1052, a PET image is reconstructed according to the second PET-scan data.

At step S1062, at least one scanning parameter is determined according to the PET image.

At step S1072, another PET scan is performed on the target region of the scanned object according to the scanning parameter to acquire third PET-scan data.

Where, step S1042 and step S1052 and step S1041 and S1051 are identical respectively, and not described repeatedly in this embodiment.

In the present embodiment, since tracer intakes of different tissues and organs are different, and the tracer fluorodeoxy-D-glucose (FDG) intakes of pathological organs and tissues, such as lung cancer and liver cancer are high. Therefore, after the PET image is acquired, the metabolic conditions of the scanned object are clearly displayed on the PET image, and at least one scanning parameter may be determined for the secondary scanning based on the position and the concentration of the tracer accumulated in the scanned object shown in the PET image. For example, it is possible to distinguish benign and malignant tumors based on the tracer intakes of diseased tissues. When there is a nodule in the lung, if there is little or no tracer intake at the corresponding location in the lung, the metabolic activity of the nodule is low, and the possibility of a benign lesion is high. On the contrary, if this nodule has an increased metabolic activity, there is a potential for malignancy.

Where, the scanning parameter may be at least one of a scanning range, a scanning time, a number of scans, a position of the scanning table, and the like, or any combination thereof. By determining at least one scanning parameter according to the PET image, target a specific organ or tissue may be targeted during the secondary scan, thereby improving the quality of the scanned data of the secondary scan, which has a higher reference significance for clinical diagnosis.

On the basis of the above embodiments, in some of these embodiments of the method, the target region includes a partial region of the scanned object. Since the position of the scanning table needs to be adjusted for scanning, it is generally suitable to scan the partial region of the scanned object.

It should be noted that the steps shown in the process above or in the flow chart of the accompanying drawings may be executed, for example, in a computer system including a set of computer-executable instructions. Although a logical order is shown in the flow chart, in some cases, the shown or described steps may be performed in an order different from one described herein.

The embodiments also provide a device of dynamic PET scanning, and the device is used to implement the foregoing embodiments and optional implementation manners. What have been described will not be repeated. As used herein, the terms "module", "unit", "subunit", and the like, may be a combination of a software and/or a hardware that may realize a predetermined function. Although the devices described in the following embodiments are preferably implemented by a software, an implementation by hardware or by a combination of software and hardware is also possible and conceivable.

Figure 4:
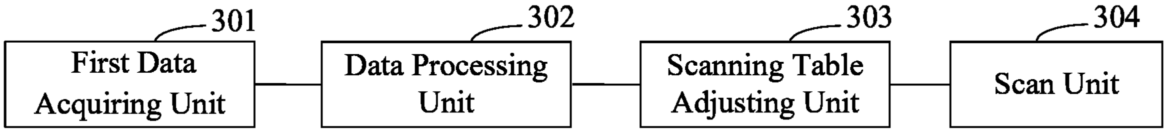
FIG. 4 is a block diagram illustrating a structure of a device of dynamic PET scanning in one of the embodiments of the present application.

FIG. 4 is a block diagram illustrating a structure of a device of dynamic PET scanning according to an embodiment of the present application. As shown in FIG. 4, the device includes: a first data acquiring unit 301, a data processing unit 302, a scanning table adjusting unit 303 and a scan unit 304

The first data acquiring unit 301 is configured to perform a PET scan on a target region of a scanned object, and acquire first PET-scan data including a single-event count received by a PET detector.

The data processing unit 302 is configured to determine a single-event count distribution in the target region according to the first PET-scan data.

The scanning table adjusting unit 303 is configured to adjust a position of a scanning table according to the single-event count distribution.

The scan unit 304 is configured to perform a PET scan on the scanned object based on the adjusted position of the scanning table.

In some of these embodiments, the first data acquiring unit 301 is further configured to acquire the first PET-scan data of the scanned object in real time or at a preset time point within a certain time period after injecting a tracer.

In some of these embodiments, the first PET-scan data include the number of coincidence events received by crystal rings at different time points. The scanning table adjusting unit 303 is further configured to adjust the position of the scanning table according to the number of coincidence events.

In some of these embodiments, the first PET-scan data include coincidence counting rates of the crystal rings at different time points. The scanning table adjusting unit 303 is further configured to adjust the position of the scanning table according to the coincidence counting rates.

In some of these embodiments, the data processing unit 302 is further configured to obtain the coincidence counting rates of at least two crystal rings within a scanning range at different time points according to the first PET-scan data, where the coincidence counting rate represents the number of coincidence events received by a single-crystal ring in the PET detector per unit time.

The scanning table adjusting unit 303 is further configured to adjust the position of the scanning table according to the coincidence counting rates.

In some of these embodiments, the scanning table adjusting unit 303 is further configured to determine whether the coincidence counting rate of the crystal ring is greater than a preset threshold value or not, and adjust the position of the scanning table according to a position of a crystal ring having the coincidence counting rate greater than the preset threshold value.

In some of these embodiments, the scanning table adjusting unit 303 is further configured to determine a maximum coincidence counting rate of the crystal ring; and configured to adjust the position of the scanning table according to a position of a crystal ring having the maximum coincidence counting rate.

In some of these embodiments, the scanning table adjusting unit 303 is further configured to move a position of a scanned object part, which corresponds to the crystal ring having the coincidence counting rate greater than the preset threshold value, to a scanning center of a PET system.

In some of these embodiments, at a last position among multiple positions of the scanning table, the scanning range at least includes a region of interest of the scanned object.

In some of these embodiments, at the last position among the multiple positions of the scanning table, a geometric center of the region of interest of the scanned object is at the scanning center of the PET system.

In some of these embodiments, the region of interest includes a heart position of the scanned object.

In some of these embodiments, the scanning table adjusting unit 303 is further configured to acquire the region of interest, and adjust the position of the scanning table according to a position of the region of interest and a position of the target region.

In some of these embodiments, the device of dynamic PET scanning further includes: a second data acquiring unit, a PET image reconstruction unit, and a PET parametric image acquiring unit.

The second data acquiring unit is configured to perform a PET scan on the target region of the scanned object at a plurality of positions of the scanning table to acquire second PET-scan data.

The PET image reconstruction unit is configured to reconstruct a PET image according to the second PET-scan data.

The PET parametric image acquiring unit is configured to acquire a PET parametric image according to the PET image.

In some of these embodiments, the device of dynamic PET scanning further includes: a second data acquiring unit, a PET image reconstruction unit, a scanning parameter determining unit, and a third data acquiring unit.

The second data acquiring unit is configured to perform a PET scan on the target region of the scanned object at a plurality of positions of the scanning table to acquire a second PET-scan data.

The PET image reconstruction unit is configured to reconstruct a PET image according to the second PET-scan data.

The scanning parameter determining unit is configured to determine at least one scanning parameter according to the PET image.

The third data acquiring unit is configured to perform another PET scan on the target region of the scanned object according to the scanning parameter to acquire third PET-scan data.

It should be noted that each of the modules may be a function module or a program module, and may be realized by software or by hardware. For the modules implemented by hardware, all of the modules above may be located in the same processor, or the modules above may be located in different processors in the form of any combination.

Figure 5:
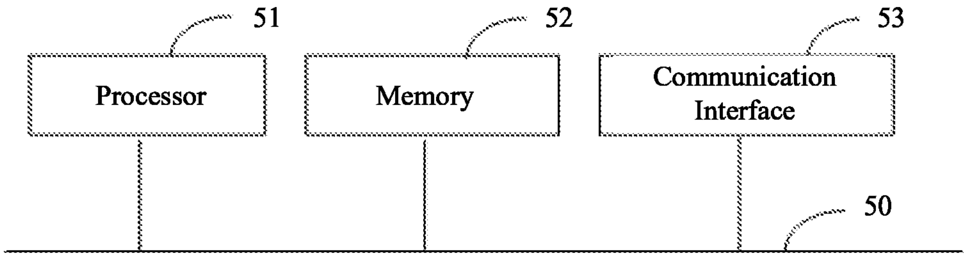
FIG. 5 is a schematic diagram illustrating a structure of a computer apparatus in one of the embodiments of the present application.

In addition, the method of dynamic PET scanning of the embodiment of the present application described in combination with FIG. 1 may be implemented by a computer apparatus. FIG. 5 is a schematic view illustrating a hardware structure of a computer apparatus according to an embodiment of the present application.

The computer apparatus may include a processor 51, and a memory 52 storing computer program instructions.

Specifically, the processor 51 may include a central processing unit (CPU), or an application specific integrated circuit (ASIC for short), or may be configured to be one or more integrated circuits which implement the embodiments of the present application.

The memory 52 may include a mass memory for data or instructions. The memory 52 may include, for example but is not limited to, a hard disk drive (HDD for short), a floppy disk drive, a solid state drive (SSD for short), a flash memory, an optical disk, a magneto-optical disk, a magnetic tape, or a universal serial bus (USB for short) driver, or a combination of two or more of what listed above. In a proper situation, the storage 52 may include removable or non-removable (or fixed) media. In a proper situation, the memory 52 may be arranged inside or outside the data processing device. In a particular embodiment, the memory 52 is a non-volatile memory. In a specific embodiment, the memory 52 includes a read-only memory (ROM for short) and a random-access memory (RAM for short). In a proper situation, the ROM may be a mask-programmed ROM, a programmable read-only memory (PROM for short), an erasable programmable read-only memory (EPROM for short), an electrically erasable programmable read-only memory (EEPROM for short), an electrically alterable read-only memory (EAROM for short), or a flash memory, or a combination of two or more of what listed above. In a proper situation, the RAM may be a static random-access memory (SRAM for short), or a dynamic random-access memory (DRAM for short). The DRAM may be a fast page mode dynamic random-access memory (FPMDRAM for short), an extended data out dynamic random-access memory (EDODRAM for short), a synchronous dynamic random-access memory (SDRAM for short), etc.

The memory 52 is configured to store or cache various data files that need to be processed and/or communicated, as well as computer program instructions executed by the processor 51 possibly.

The processor 51 may implement any one of the methods of dynamic PET scanning in the embodiments above by reading and executing the computer program instructions stored in the memory 52.

In some of these embodiments, the computer device may further include a communication interface 53 and a bus 50. As shown in FIG. 5, the processor 51, the memory 52, and the communication interface 53 are connected through the bus 50 to complete mutual communication.

The communication interface 53 is configured to realize the communication between various modules, devices, units and/or devices in the embodiments of the present application. The communication interface 53 may also implement data communication with other components such as external devices, image/data acquisition equipment, databases, external storage, and image/data processing workstations.

The bus 50 includes a hardware, a software, or both the hardware and the software, and the components of the computer apparatus are coupled to each other. The bus 50 includes but is not limited to at least one of the following: a data bus, an address bus, a control bus, an expansion bus, and a local bus. The bus 50 may include, for example but is not limited to, an accelerated graphics port (AGP for short) or other graphics bus, an enhanced industry standard architecture (EISA for short) bus, a front side bus (FSB for short), a hyper transport (HT for short) interconnection, an industry standard architecture (ISA for short) bus, an infinite bandwidth (InfiniBand for short) interconnection, a low pin count (LPC for short) bus, a memory bus, a micro channel architecture (MCA for short) bus, a peripheral component interconnect (PCI) bus, a PCI-Express (PCI-X) bus, a serial advanced technology attachment (SATA for short) bus, a video electronics standards association local bus (VLB for short), or other suitable bus, or a combination of two or more of these buses. In a proper situation, the bus 50 may include one or more buses. Although particular buses are described and illustrated in the embodiments of this application, any suitable bus or interconnect may be contemplated in this application.

The computer apparatus may execute the method of dynamic PET scanning in the embodiments of the present application based on the acquired computer program instructions, thereby realizing the method of dynamic PET scanning described in combination with FIG. 1 to FIG. 3.

In addition, combining with the method of dynamic PET scanning in the foregoing embodiments, the embodiments of the present application may provide a computer-readable storage medium to implement the method of dynamic PET scanning Computer program instructions are stored on the computer-readable storage medium. When executed by a processor, the computer program instructions perform any one of the methods of dynamic PET scanning in the embodiments above.

The technical features of the embodiments above may be combined arbitrarily. To make the description concise, not all possible combinations of the technical features in the above embodiments are described. However, as long as there are no contradictions in the combinations of these technical features, all of the combinations should be considered to be within the scope of the specification.

The embodiments above only represent several implementation modes of the present application, and the description thereof is relatively specific and detailed, but it should not be construed as limiting the scope of the patent. It should be noted that for those skilled in the art, various modifications and improvements may be made without departing from the concept of the present application, and all these modifications and improvements belong to the protection scope of the present application. Therefore, the scope of protection of the patent application should be subject to the appended claims.

What is claimed is:

1. A method of dynamic PET scanning, comprising:

performing a PET scan on a target region of a scanned object, and acquiring first PET-scan data, the first PET-scan data comprising a single-event count received by a PET detector;

determining a single-event count distribution in the target region according to the first PET-scan data;

adjusting a position of a scanning table according to the single-event count distribution; and performing a PET scan on the scanned object according to the adjusted position of the scanning table.

2. The method of dynamic PET scanning according to claim 1, wherein the acquiring the first PET-scan data comprises:

acquiring the first PET-scan data of the scanned object in real time or at a preset time point within a certain time period after injecting a tracer.

3. A method of dynamic PET scanning, comprising:

performing a PET scan on a target region of a scanned object, and acquiring first PET-scan data, the first PET-scan data comprising the number of coincidence events received by crystal rings at different time points;

adjusting a position of a scanning table according to the number of coincidence events; and performing a PET scan on the scanned object according to the adjusted position of the scanning table;

wherein the first PET-scan data comprise coincidence counting rates of the crystal rings at different time points; each of the coincidence counting rates represents the number of coincidence events received by a single-crystal ring in a PET detector per unit time; and the adjusting the position of the scanning table according to the number of coincidence events comprises:

adjusting the position of the scanning table according to the coincidence counting rates.

4. The method of dynamic PET scanning according to claim 3, wherein the adjusting the position of the scanning table according to the coincidence counting rates comprises:

determining whether a coincidence counting rate of each of the crystal rings is greater than a preset threshold value or not; and adjusting the position of the scanning table according to a position of a crystal ring having the coincidence counting rate greater than the preset threshold value.

5. The method of dynamic PET scanning according to claim 3, wherein the adjusting the position of the scanning table according to the coincidence counting rates comprises:

determining a maximum coincidence counting rate of the crystal rings; and adjusting the position of the scanning table according to a position of a crystal ring having the maximum coincidence counting rate.

6. The method of dynamic PET scanning according to claim 4, wherein the adjusting the position of the scanning table according to the position of the crystal ring having the coincidence counting rate greater than the preset threshold value, comprises:

moving a position of a scanned object part, which corresponds to the crystal ring having the coincidence counting rate greater than the preset threshold value, to a scanning center.

7. The method of dynamic PET scanning according to claim 1, wherein at a last position among multiple positions of the scanning table, a scanning range at least comprises a region of interest of the scanned object.

8. The method of dynamic PET scanning according to claim 7, wherein at the last position among the multiple positions of the scanning table, a geometric center of the region of interest of the scanned object is at a scanning center.

9. The method of dynamic PET scanning according to claim 8, wherein the region of interest comprises a heart position of the scanned object.

10. The method of dynamic PET scanning according to claim 1, further comprising:

acquiring a region of interest, and adjusting the position of the scanning table according to a position of the region of interest and a position of the target region.

11. The method of dynamic PET scanning according to claim 1, further comprising:

performing a PET scan on the target region of the scanned object at a plurality of positions of the scanning table to acquire second PET-scan data;

reconstructing a PET image according to the second PET-scan data; and acquiring a PET parametric image according to the PET image.

12. The method of dynamic PET scanning according to claim 1, further comprising:

performing a PET scan on the target region of the scanned object at a plurality of positions of the scanning table to acquire second PET-scan data;

reconstructing a PET image according to the second PET-scan data;

determining at least one scanning parameter according to the PET image; and performing another PET scan on the target region of the scanned object according to the scanning parameter to acquire third PET-scan data.

13. The method of dynamic PET scanning according to claim 1, wherein the target region comprises a partial region of the scanned object.

14. A device of dynamic PET scanning, comprising:

a first data acquiring unit, configured to perform a PET scan on a target region of a scanned object, and acquire first PET-scan data, wherein the first PET-scan data comprises a single-event count received by a PET detector;

a data processing unit, configured to determine a single-event count distribution in the target region according to the first PET-scan data;

a scanning table adjusting unit, configured to adjust a position of a scanning table according to the single-event count distribution; and a scan unit, configured to perform a PET scan on the scanned object according to the adjusted position of the scanning table.

15. A computer apparatus, comprising a memory, a processor, and a computer program stored in the memory and executable by the processor, wherein the processor, when executing the computer program, performs the method of dynamic PET scanning according to claim 1.

16. A computer apparatus, comprising a memory, a processor, and a computer program stored in the memory and executable by the processor, wherein the processor, when executing the computer program, performs the method of dynamic PET scanning according to claim 3.

17. The method of dynamic PET scanning according to claim 7, wherein the acquiring the first PET-scan data comprises: acquiring the first PET-scan data of the scanned object in real time or at a preset time point within a certain time period after injecting a tracer.

18. The method of dynamic PET scanning according to claim 5, wherein a maximum value among the coincidence counting rates of the crystal rings is selected as the maximum coincidence counting rate.

19. The method of dynamic PET scanning according to claim 6, wherein, before the moving the position of the scanned object part, which corresponds to the crystal ring having the coincidence counting rate greater than the preset threshold value, to the scanning center, the method further comprises: based on position information of the crystal ring receiving photons and corresponding photon information, determining the position of the scanned object part, which corresponds to the crystal ring having the coincidence counting rate greater than the preset threshold value.

* * * * *